United States Patent [19]
Shaw

[11] Patent Number: 5,248,056
[45] Date of Patent: Sep. 28, 1993

[54] DISPOSABLE RESERVOIR

[75] Inventor: James D. Shaw, Hilton, N.Y.

[73] Assignee: Eastman Kodak Company, Rochester, N.Y.

[21] Appl. No.: 869,279

[22] Filed: Apr. 15, 1992

[51] Int. Cl.⁵ ............................................ B65D 43/14
[52] U.S. Cl. .................................... 220/331; 220/264; 220/335; 220/343; 220/344; 220/367; 220/369; 220/410; 215/238; 215/241; 215/307
[58] Field of Search ............... 220/253, 259, 263, 264, 220/331, 335, 343, 344, 367, 369, 410; 215/238, 240, 241, 244, 307

[56] References Cited

U.S. PATENT DOCUMENTS

| | | | |
|---|---|---|---|
| 636,801 | 11/1899 | Hövermann | 215/241 |
| 677,192 | 6/1901 | Feldmann | 215/241 |
| 1,162,791 | 12/1915 | Lubas . | |
| 1,482,534 | 2/1924 | Woodbridge . | |
| 1,725,092 | 8/1929 | Lowy | 215/307 X |
| 2,145,739 | 3/1936 | Shaw . | |
| 4,192,435 | 3/1980 | Volpelier | 220/331 |
| 4,343,397 | 8/1982 | Nozawa et al. | 220/335 X |
| 4,543,889 | 10/1985 | Fritz . | |
| 4,740,274 | 4/1988 | Kissel . | |
| 4,742,928 | 5/1988 | Braun | 220/335 X |
| 4,956,156 | 9/1990 | Kanner et al. | 220/367 X |

FOREIGN PATENT DOCUMENTS

| | | | |
|---|---|---|---|
| 63230 | 10/1982 | European Pat. Off. | 220/335 |
| 252556 | 9/1911 | Fed. Rep. of Germany | 220/335 |
| 3429050 | 2/1986 | Fed. Rep. of Germany | 220/259 |

Primary Examiner—Stephen P. Garbe
Assistant Examiner—Stephen Cronin
Attorney, Agent, or Firm—Dana M. Schmidt

[57] ABSTRACT

A covered reservoir is disclosed comprising a reservoir body, a holder for the body, a cover, a retainer for the cover, and a seal fitted onto the cover to seal off leak paths between the cover and the reservoir body. The cover is constructed to raise the seal into a frusto-conical position, preferably via a frusto-conical surface on which the seal, which is a flexible annular ring, is seated.

9 Claims, 3 Drawing Sheets

5,248,056

DISPOSABLE RESERVOIR

FIELD OF THE INVENTION

This invention relates to covered reservoirs as are used in, e.g., clinical analyzers to provide liquids needed, for example, reference liquids.

BACKGROUND OF THE INVENTION

Reference liquids are used in many clinical analyzers to conduct potentiometric tests using twin ion-selective electrodes. One of those electrodes is contacted with the patient sample having an ion of unknown concentration, and the other electrode is contacted with the reference liquid having a known concentration of ions. Most preferably, such ions are highly concentrated to the point of near saturation, for the reason that the junction potential between the reference liquid and the sample needs to be dominated by the reference liquid concentration, which means the latter must be highly concentrated. The reference liquid is stored in a reservoir that has to be replenished. See, e.g., U.S. Pat. No. 4,740,274 for further details on the reference liquid.

For years the most common reservoir for such a reference liquid has been a glass or plastic vial that is capped with a rubber seal that is machine-opened and closed. Before the vial is replenished, it has to be removed and cleaned to maintain an accurate concentration of the ions. Such a procedure has been a problem because it is time-consuming, labor intensive, and if not done properly, introduces errors due to the concentration of the liquid being altered.

There has therefore been a long-standing need for a disposable, single-use reservoir which, although preventing evaporation, readily allows access to the liquid by an aspirator. "Single-use" as used here means used until the liquid contents of the reservoir have been exhausted without replenishment.

The most obvious solution to the need was to form the reservoir as a simple plastic body with an aperture at the top sized to seal on the aspirator when it is inserted. In that fashion, the aspirator acts as a stopper when it is kept in the reservoir aperture when no reference liquid is being dispensed in the analyzer. However, it was soon discovered that this design was unsatisfactory because insertion of the aspirator into its sealing position created severe pumping action in the reservoir due to flexing of the top of the reservoir that interfered with pressure sensing that is otherwise necessary with such aspirators.

The next step was to enlarge slightly the aperture for the aspirator, so that a complete seal, and hence pumping, did not occur due to the "leak" created. The aperture could not be made too large, however, as evaporation then is too substantial. However, this was found to be a failure in that the "leak" portion of the aperture created a sufficient capillary path for liquid when it sloshed, as to cause unacceptable crusting of the high salts contents of the liquid at that "leak" portion.

Next, a flat cover, apertured for the aspirator, was designed to fit over and close off the top of the reservoir. However, this sealed to the top of the reservoir along a flat surface. The flat cover attempted to achieve controlled venting by a long diffusion path between the cover and reservoir. However, economical manufacturing tolerances would not allow the gap to be controlled tightly enough to prevent excessive evaporation in worst case conditions.

Thus, for many months, attempts have been made to create an acceptable disposable alternative for the permanent glass reference liquid reservoir heretofore used, all without success.

SUMMARY OF THE INVENTION

I have designed a disposable reservoir with a cover that finally solves the problems noted above.

More specifically, there is provided a covered reservoir for providing liquid to a pipette through an opening, the reservoir comprising a body for holding the liquid in bulk, the body terminating in a upper, generally flat rim extending out over a portion the body and an aperture left open by the rim; a cover having an aperture therein for accessing the liquid with a pipette and a contact surface for contacting the rim; a seal disposed between the cover and the body to restrict evaporation; and means for biasing the cover against the seal and the body. The cover further includes a) a generally planar recess adjacent to the cover contact surface of a size and shape effective to receive the seal between the cover and the rim without clamping it, b) a shoulder depending from the recess and surrounding the aperture and around which the seal is mounted, the shoulder having an outside diameter sufficient to friction fit it with the annular ring seal, and c) raising means joining the shoulder to the recess and surrounding the shoulder, for raising the annular ring seal from the recess into a frusto-conical position sufficient to cause said rim at the rim aperture to press into the annular ring seal when the cover contacts the rim.

Accordingly, it is an advantageous feature of the invention that a cover is provided for a disposable reservoir for pipette access, that seals against the reservoir body in a manner that reduces evaporation while at the same time preventing "pumping" and salt formation due to liquid contact.

Another advantageous feature of the invention is that the parts of the cover are readily removable for cleaning.

Other advantageous features will become apparent with reference to the following detailed description, when read in light of the attached drawings.

DESCRIPTION OF THE PREFERRED EMBODIMENTS

The following description relates to the invention in its preferred embodiment, wherein a saturated salt solution is contained in a disposable reservoir container, using a cover removably held on a retainer that is bi-stably and pivotally mounted onto the frame holding the container with a spring that tends to bias the cover closed. In addition, the invention is useful regardless of the liquid held in the reservoir, whether it is disposable or not, and regardless of how the cover is retained on the reservoir, so long as it has the seal features of the invention.

Figure 1:
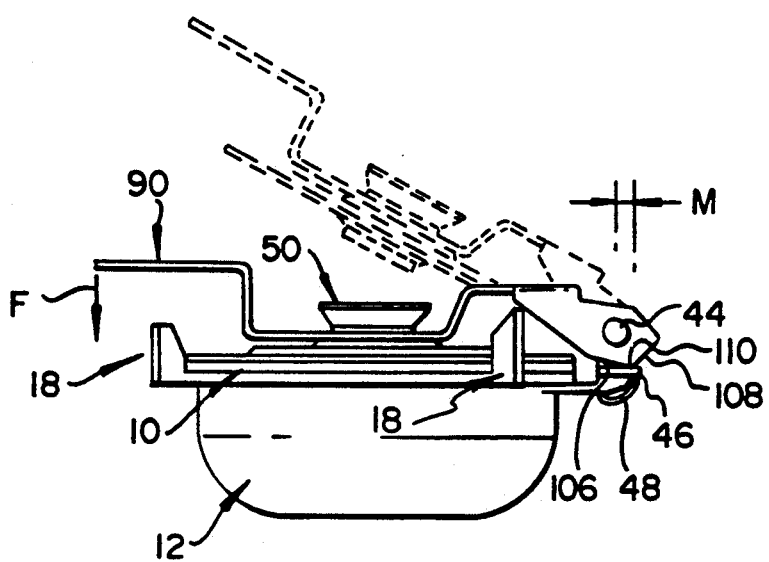
FIG. 1 is an elevational view of a reservoir constructed in accordance with the invention, the phantom lines illustrating the cover in its open position.
Figure 2:
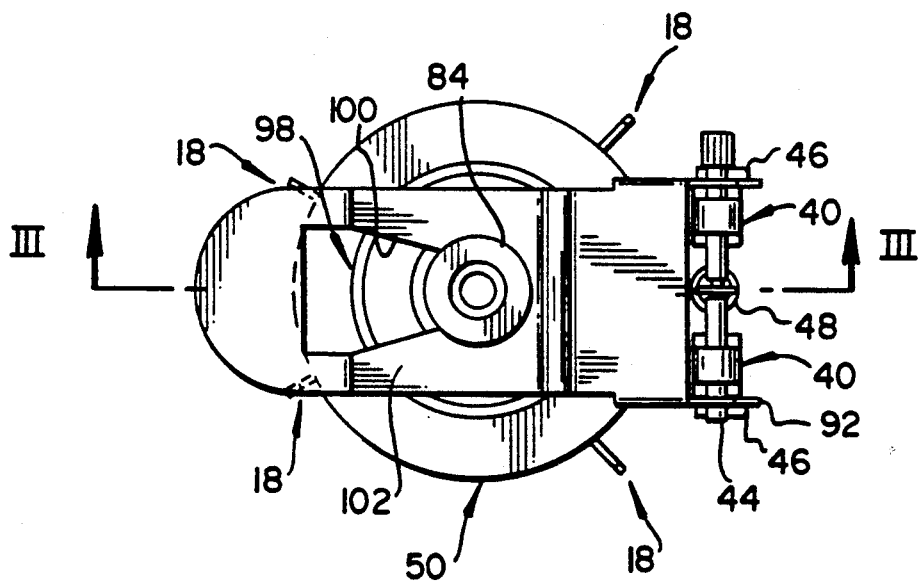
FIG. 2 is a plan view of the reservoir.
Figure 3:
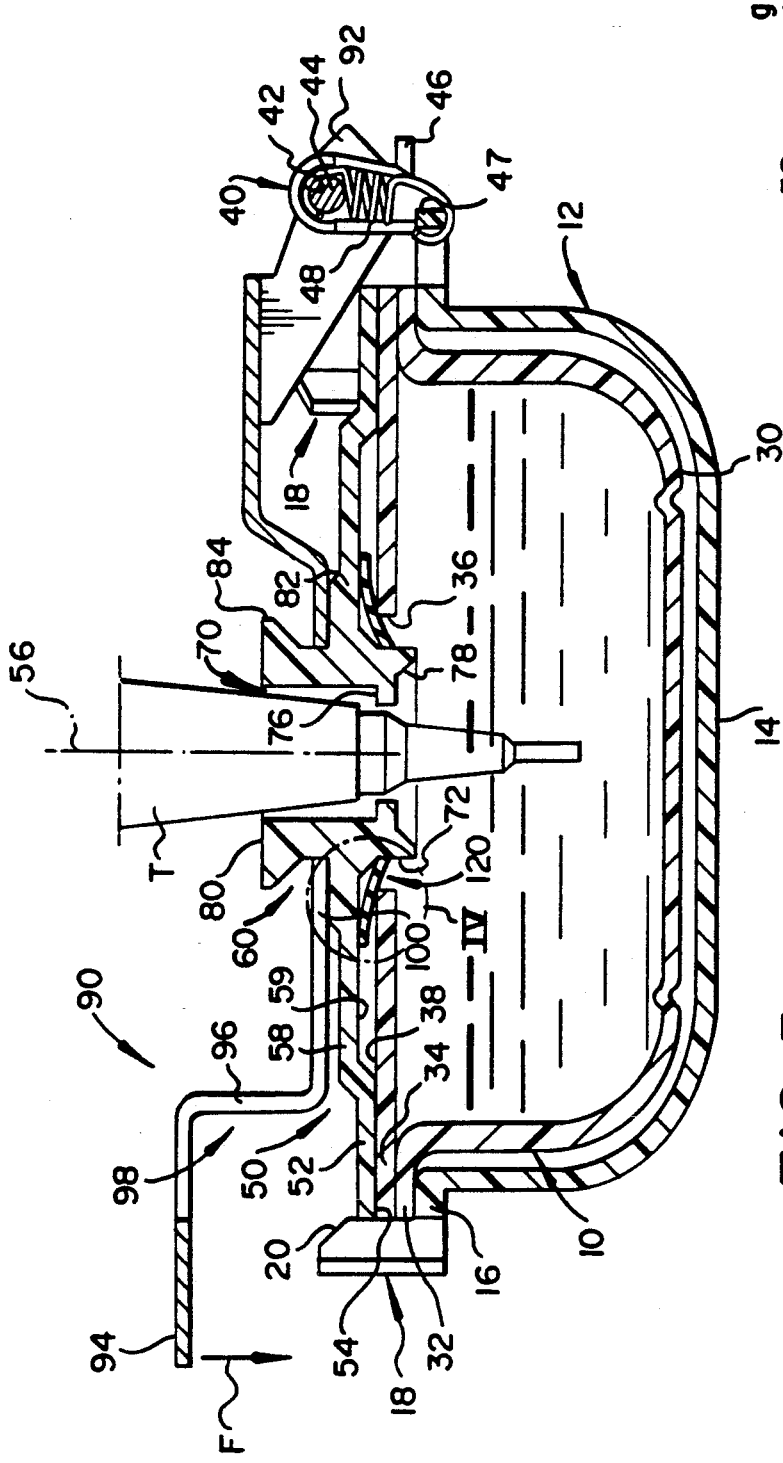
FIG. 3 is a section view taken generally along the line III—III of FIG. 2.

A covered reservoir constructed in accordance with the invention is illustrated in FIGS. 1-3. Generally it comprises a reservoir body 10, a cover 50, a cover retainer 90 and a seal 120, FIG. 3. The reservoir body 10 is preferably disposable, and sits in a housing or holder 12 shaped as a bowl, the bowl preferably having a shape that complements the shape of the reservoir body 10, as shown most clearly in FIG. 3. Thus, bowl 12 has a closed bottom wall 14 and an upper lip 16 extending preferably around its circumference, and can optionally include fastening flanges (not shown) for securing the lip and bowl to a clinical analyzer. Guide fingers 18 project upwardly from lip 16, with a guiding surface 20 sloped to center the cover when it is lowered, as explained below.

Reservoir 10 comprises body wall 30 that terminates in an upper lip 32 shaped to rest on lip 16, and a generally flat rim 34 that is sealed to the lip 32 and extends out over body wall 30 except for an access aperture 36 shaped to receive a center portion of the cover 50 of the reservoir and an aspirator tip "T" inserted therein. Exterior surface 38 of rim 34 comprises the contact surface for contact with the cover, as explained hereinafter.

To help retain cover 50, pivot lugs 40 are preferably included, FIG. 2, as part of the molded shape of bowl 12 at the back side. Specifically, FIG. 3, lugs 40 each include aperture 42 through which a pivot pin 44 extends, and ears 46 and 47 extending horizontally from lugs 40. Ears 46 act as supports for the bi-stable camming of the retainer, described below, and ear 47 is the anchor for a spring 48 that biases retainer 90 closed when the latter is properly pivoted.

Apertures 42 are larger than the diameter of pin 44, to allow the pin to raise and lower with the pivoting action of retainer 90.

Most preferably, spring 48 is a tension spring with a spring constant sufficient to provide no more than about 60 g (⅛ pounds) of spring force downwardly on retainer 90 at end 94, FIG. 3, as shown by force "F." Any spring force significantly greater than that will tend to cause splashing of the liquid, which in turn can cause loss of liquid or crusting of the cover. Also, it would cause a "snap" that can startle the operator working inside the analyzer.

Cover 50 comprises preferably a fairly rigid disk the outer circumference of which is a generally flat flange 52 having a bottom contact surface 54 for contacting rim 34. The disk is preferably symmetric about a center axis 56. Inside of and adjacent to flange 52, closer to axis 56, is a generally planar annular recess portion 58, the depth d of the recess measured from surface 54 to surface 59 of portion 58, FIG. 4, being more than the thickness of seal 120, described below. Still further in towards axis 56 is a shoulder 60 that extends out of the plane of flange 52 and recess portion 58, preferably in both directions, which shoulder in turn surrounds an access and aperture 70 on axis 56, into which tip T is inserted, FIG. 3.

Shoulder 60 comprises a lower portion 72 and an upper portion 80. Lower portion 72 an outside diameter that cooperates with seal 120 to friction fit the seal around the shoulder, FIG. 4, and is integrally joined to surface 59 of recessed portion 58 by a frusto-conical surface 74 that extends entirely around axis 56. Surface 74 is shaped to space or raise seal 120 off surface 59. To that end, the height of surface 74, measured along axis 56, is generally equal to depth "d."

Additionally, lower portion 72 includes means for inducing condensed vapor to flow back into reservoir body 10, rather than to evaporate out aperture 70. Specifically, FIG. 3, a flange 76 extends out from lower portion 72 towards axis 56, to form a seat for pipette tip T. Where flange 76 joins portion 72, its bottom surface is sloped downwardly at 78 to provide a run-off surface for condensation.

Upper portion 80 of shoulder 60 includes a raised boss 82 used to help seat retainer 90, discussed below at the correct height, and an engaging flange 84 designed to slip through slot 98 of retainer 90, FIG. 2, thus holding cover 50 within the retainer.

Conventional rigid plastics are preferably used to mold cover 50. To provide sufficient rigidity, the thickness of recessed portion 58, FIG. 3, can be, for example, about 1.5 mm.

To removably hold the cover 50 onto reservoir body 10, a retainer 90 is hingedly mounted on pin 44 at retainer end 92, FIG. 3. Opposite end 94 is a handle portion, bent upward at portion 96 to form an L-shape for easier grasping. Portion 96 is slotted at 98, as best shown in FIG. 2, slot 98 being narrowed at 100 on portion 102 of retainer 90 that sits on boss 82, so as to lock in engaging flange 84 when cover 50 is slid to the rear of retainer 90.

End 92 of retainer 90 provides the bi-stable positioning of retainer 90, in cooperation with ears 46 and spring 48. Specifically, end 92 is provided with two camming surfaces 106 and 108, FIG. 1, that contact ears 46 alternately, as end 92 is pivoted on pin 44 about its pivot point 110 between surfaces 106 and 108.

Figure 4:
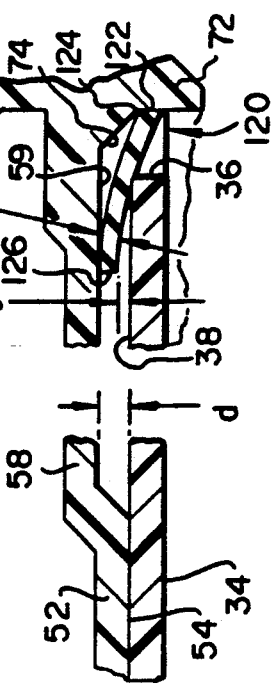
FIG. 4 is an enlarged fragmentary section view of the portion of FIG. 3 marked as "IV.

Seal 120, FIGS. 3 and 4, is preferably an annular seal of flexible material, such as rubber or synthetic plastics. Whatever the material, it is preferably at least as elastic and flexible as a silicone rubber having a 30 Shore A Durometer value. The inside diameter 122, FIG. 4, is such as provides a friction fit of the seal over shoulder 60 and specifically causes it to rest at edge 124 of surface 74 The thickness "$d_1$" of the seal is sufficiently less than dimension "d," that is, by amount "g," such that when cover 50 closes into contact with reservoir body 10, the contact is via flange 52 on surface 38, and outside diameter 126 of seal 120 is not clamped between surface 59 and surface 38. (For example, "$d_1$" can be about 0.8 mm and recess depth "d" can be about 1.3 mm.) Because of the rigidity of the plastic of flange 52 and recessed portion 58, this ensures that the force of pipette tip T contacting shoulder 60 is absorbed by cover flange 52, thus minimizing or eliminating any pumping action, due to the rigidity of the cover. Comparatively, if seal 120 had a thickness "$d_1$" that equals or exceeds gap "d," then the contact force of tip T would be transmitted at seal 120, the moment arm of flange of 52 would be ineffective to absorb that shock, and "pumping" would likely occur.

The softness and/or flexibility of seal 120, as well as its raised frusto-conical position on the edge 124 of surface 74, FIG. 4, ensure that, upon closure of cover 50 onto reservoir body 10, aperture edge 36 of rim 34, pushes into seal 120, around the entire circumference of shoulder 60, thus sealing off what would otherwise be an evaporation path out between surfaces 38 and 59.

Figure 5:
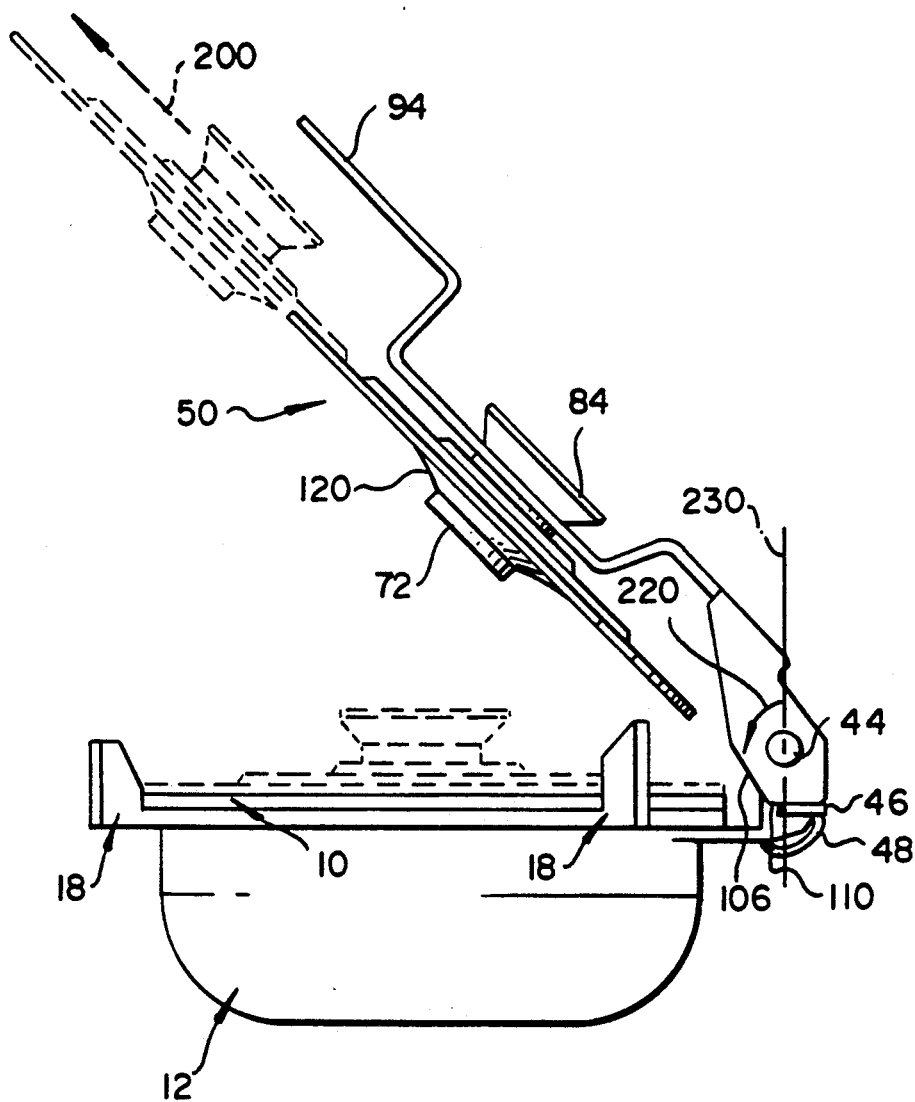
" and FIG. 5 is an elevational view similar to that of FIG. 1 but showing the cover raised to its open position, and the cover being removed in phantom.

The reservoir cover's use and functions will be readily apparent from the previous description. Briefly, cover 50 is removed and replaced, arrow 200, FIG. 5, by sliding shoulder 60 and flange 84 out and in through slot 98, respectively, FIG. 3. Once in place in retainer 90, the retainer is pivoted, FIG. 1, arrow 220, by grasping handle portion 94. This causes end portion 92 to pivot about point 110, raising retainer 90 slightly, until the point 110 passes behind vertical line 230 of pivot pin 44. At this point, spring 48, FIG. 3, is effective to pull the retainer and cover shut, with surface 106, FIG. 1, resting or almost resting on ear 46 and seal 120 closing off aperture 36, FIG. 4. Guide fingers 18, FIGS. 1 and 2, are effective to properly guide and center cover 50 as it closes onto reservoir body 10. The spring action of spring 48, FIG. 3, acts through moment arm "M," FIG. 1, to deliver closure force F, FIGS. 1 and 3, on handle portion 94 (discussed above).

Although it is true that aperture 70 becomes a leak path when tip T is removed, this path occurs only temporarily, during dispensing of the liquid, and thus is not as much of a leakage compared to any path between surfaces 38 and 59 that is unblocked by seal 120.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. A covered reservoir for providing liquid to a pipette through an opening, the reservoir comprising a body for holding the liquid in bulk, said body terminating in a upper, generally flat rim extending out over a portion of the body and an aperture left open by said rim; a cover having an aperture therein for accessing the liquid with a pipette and a contact surface for contacting said rim; a flexible annular ring seal disposed between said cover and said body to restrict evaporation; and means for biasing said cover against said seal and said body;

said cover including a) a generally planar recess adjacent to said contact surface of a size and shape effective to receive said seal between said cover and said rim without clamping it, b) a shoulder depending from said recess and surrounding said aperture and around which said seal is mounted, said shoulder having an outside diameter sufficient to friction fit it with said annular ring seal, and c) spacing means joining said shoulder to said recess and surrounding said shoulder, for spacing said annular ring seal from said recess into a frusto-conical position sufficient to cause said rim at said rim aperture to press into said annular ring seal when said cover contacts said rim.

2. A covered reservoir as defined in claim 1, wherein said spacing means comprise a frusto-conical surface integral with said shoulder and said recess, extending around said aperture, with a height measured from said recess that is about equal to the depth of said recess.

3. A covered reservoir as defined in claim 2, wherein one surface of said ring seal is seated on said frusto-conical surface at the intersection of said frusto-conical surface and said shoulder, so that when said cover is closed, said rim of said body contacts at said rim aperture a surface of said seal opposite to said one surface.

4. A covered reservoir as defined in claim 1, wherein said shoulder includes means surrounding said aperture for inducing condensed vapor on said cover to flow back into said body.

5. A covered reservoir as defined in claim 1, wherein said biasing means include means for removably holding said cover with respect to said reservoir, said holding means being pivotally mounted on said reservoir body and including a slot into which said cover can be slid.

6. A covered reservoir as defined in claim 5, wherein said holding means includes a bi-stable cam for camming said cover either open or closed with respect to said reservoir body, said biasing means being effective to urge said cover into said closed position when said cam permits it.

7. A covered reservoir as defined in claim 5, and further including guiding means on said reservoir for guiding said cover aperture into alignment with said rim aperture.

8. A covered reservoir as defined in claim 1, and further including a manual handle on said biasing means, and wherein said biasing means acts with a closing force, measured at said handle, that is no greater than about 60g ($\frac{1}{8}$ lb. force).

9. A covered reservoir for providing liquid to a pipette through an opening, the reservoir comprising a body for holding the liquid in bulk, said body terminating on an upper, generally flat rim extending out over the body with an aperture left open; a cover having an aperture therein for accessing the liquid with a pipette and a contact surface for contacting said rim; and a seal disposed between said cover and said body to restrict evaporation;

said cover including a downwardly depending shoulder around said aperture with means for drawing condensed moisture away from said aperture, a recessed flat annular surface stepped upwardly away from said contact surface, and an a frusto-conical surface joining said recess to said shoulder and having a depth generally equal to the depth of said recessed surface, said seal comprising a flexible annular ring with an inside diameter sufficient to allow said ring to snugly fit around said shoulder on said frusto-conical surface, and a thickness less than the depth of said recess within said cover, and wherein said reservoir further includes means for biasing said cover to press against said seal when said cover contacts said rim, so that said annular ring is depressed by said rim aperture when said body rim is pressed against said cover contact surface.

* * * * *